(12) United States Patent
Bizzarri et al.

(10) Patent No.: US 7,943,910 B2
(45) Date of Patent: May 17, 2011

(54) METHOD AND DEVICE FOR DETERMINING THE FLUORESCENCE OF A SAMPLE AND USE THEREOF

(75) Inventors: Alessandro Bizzarri, Graz (AT); Christian Konrad, Graz (AT); Volker Ribitsch, Graz (AT)

(73) Assignee: Joanneum Research Forschungsgesellschaft mbH, Graz (AT)

( * ) Notice: Subject to any disclaimer, the term of this patent is extended or adjusted under 35 U.S.C. 154(b) by 251 days.

(21) Appl. No.: 12/086,004

(22) PCT Filed: Dec. 15, 2006

(86) PCT No.: PCT/AT2006/000517
§ 371 (c)(1),
(2), (4) Date: Jun. 4, 2008

(87) PCT Pub. No.: WO2007/068021
PCT Pub. Date: Jun. 21, 2007

(65) Prior Publication Data
US 2009/0283681 A1    Nov. 19, 2009

(30) Foreign Application Priority Data
Dec. 16, 2005   (AT) .................................. A 2014/2005

(51) Int. Cl.
*G01J 3/433*   (2006.01)
(52) U.S. Cl. .................................................. 250/459.1
(58) Field of Classification Search ............. 250/339.06, 250/341.1, 341.7, 363.01, 365, 393, 459.1, 250/461.1
See application file for complete search history.

(56) References Cited

U.S. PATENT DOCUMENTS

| 4,099,872 A | 7/1978 | White |
| 4,661,711 A | 4/1987 | Harjunmaa |
| 5,196,709 A | 3/1993 | Berndt et al. |
| 6,157,037 A * | 12/2000 | Danielson .................. 250/458.1 |
| 6,673,626 B1 * | 1/2004 | Rabinovich et al. .......... 436/172 |
| 2009/0283699 A1 * | 11/2009 | Baltz et al. ................. 250/459.1 |
| 2010/0006773 A1 * | 1/2010 | Aasmul ...................... 250/459.1 |
| 2010/0230614 A1 * | 9/2010 | Lear et al. .................. 250/459.1 |

FOREIGN PATENT DOCUMENTS

| DE | 229 220 | 10/1985 |
| DE | 198 49 585 | 5/2000 |
| GB | 1 596 522 | 8/1981 |

OTHER PUBLICATIONS

International Search Report dated Mar. 12, 2007.

* cited by examiner

*Primary Examiner* — David P Porta
*Assistant Examiner* — David S Baker
(74) *Attorney, Agent, or Firm* — Jacobson Holman PLLC

(57) ABSTRACT

In a method and a device for determining the fluorescence of a sample, wherein the sample (40) is irradiated by light (25) of a wavelength which is suitable to excite fluorescent light (27, 28) in the sample and the fluorescent light (28) emitted by the sample is received in a receiver (24) and converted into a measurement signal, wherein reference light (32) in particular for compensating for ambient influences is additionally fed to the receiver (24) and likewise converted into a reference measurement signal, provision is made for the optical path of the excitation light (25) entering the sample (40) and fluorescent light (27, 28) leaving the sample (40) to be separated from the optical path (32) of the reference light having the same wavelength as the excitation light between light sources (21, 31) and receiver (24), by means of which a more precise evaluation of the fluorescent light emitted by a sample (40) can be achieved in addition to a simplified design complexity.

13 Claims, 3 Drawing Sheets

METHOD AND DEVICE FOR DETERMINING THE FLUORESCENCE OF A SAMPLE AND USE THEREOF

This is a national stage of International Application No. PCT/AT2006/000517 filed on Dec. 15, 2006 and published in German.

FIELD OF THE INVENTION

The present invention relates to a method for determining the fluorescence of a sample, wherein the sample is irradiated with light of a wavelength which is suitable to excite fluorescent light in the sample, and the fluorescence light emitted by the sample is received in a receiver and converted into a measurement signal, wherein reference light, in particular for compensating for ambient influences, is additionally fed to the receiver and likewise converted into a reference measurement signal. The invention further relates to a device for determining the fluorescence of a sample, including a light source for emitting light of a wavelength which is suitable to excite fluorescent light in the sample, and a receiver which receives the fluorescence light emitted by the sample and converts the same into a measurement signal, wherein reference light, in particular for compensating for ambient influences, is additionally feedable to the receiver and convertible into a reference measurement signal by the same.

PRIOR ART

In the context of the present description, the expression "a wavelength" is meant to also encompass a wavelength range located about a central and defined wavelength and, in particular, a narrow wavelength range, as is, for instance, the case when using a light diode or LED.

Such methods and devices are, for instance, known from DD-A 229 220, U.S. Pat. No. 5,196,709 or DE-C 198 49 585.

The determination of the fluorescence of specific molecules has been increasingly used in sensorial applications for determining various analytes. In doing so, the molecules are set into an excited state by being irradiated with light of a specific wavelength. The return of the molecules into the basic state is effected by the radiation of light having a higher wavelength than the excitation light (Stoke's shift). In addition, this emission is temporally shifted. Information on the sample to be determined can be obtained by measuring the intensity or the decay time of the fluorescence light. Possible applications of this phenomenon include environmental analytics, medical diagnostics, the monitoring of numerous industrial processes and laboratory analyses.

The simplest method for determining the properties of analytes through fluorescence measurements consists in the detection of the intensity of the light emitted by the fluorescent molecule. However, this method involves serious drawbacks in practical applications. Thus, the washing out or bleaching of the fluorescence dye as well as fluctuations of the light source and the non-linearity of optical detectors will have direct influence on the measurement results. While changes relating to the dye can only be compensated for by calibration with defined concentrations of the specific analyte, expensive temperature stabilizations or optical components are frequently required in terms of instrumentation in order to keep these effects as low as possible.

Another, more compact method is provided by the determination of the time delay with a dominating time constant $\tau$ of the radiated fluorescence light, which is also referred to as "useful life", "decay time" or "life time". The determination of the time constant can be effected by measuring the decay constant after pulsed excitation (in the time domain) of by measuring the phase shift in the event of sinusoidal excitation (in the frequency domain). Since the determinations of the decay time constant and phase shift, respectively, are basically independent of the emitted intensity and practically only limited by the subsequent instrumentation, dye effects (e.g. washing out, bleaching) are negligible. In practical implementations, the determination of the phase shift for the detection of changes of selective dyes has prevailed over measurements of the decay time on account of the little instrumental expenditures involved.

It is in any case recommendable, even when determining phase shifts—not the least because of the use in different environments—to perform referencing in order to compensate for temperature influences relating to the active optical components as well as the evaluation electronics. The simplest variant of realizing referencing in compliance with these objects has turned out to be the determination of a phase shift of the measuring circle without a selective dye. In doing so, switching is periodically performed between a signal light source, which determines the phase shift caused by the sample, and a reference light source, which determines the phase shift of the instrumentation, with the true phase shift being finally determined by subtracting the reference phase shift form the signal phase shift.

For applications in process technology and medical diagnostics, miniaturization, automation and low costs of such measuring systems are prerequisites for the acceptance by the user. Expensive optical arrangements involving, in particular, high-cost optical filters constitute substantial factors or disadvantages in this respect.

Regardless of any referencing methods and stabilizing techniques, the ratio of fluorescence light to excitation light is small and, hence, calls for various optical methods (optical arrangements and/or optical filters) for separating the light of these two light sources.

Departing from a method and device of the initially defined kind, the present invention aims to provide simple optical arrangements and ways of referencing, and to enable precise evaluations, in particular, by providing structurally simple and, hence, cost-effective configurations.

SUMMARY OF THE INVENTION

To solve these objects, a method of the initially defined kind is substantially characterized in that the optical path of the excitation light entering the sample and the fluorescence light leaving the sample is separated from the optical path of the reference light having the same wavelength as the excitation light, between the light sources and the receiver. By the separation of the optical path of the excitation light entering the sample and the fluorescence light leaving the sample from the optical path of the reference light, as in accordance with the present invention, it is ensured that the reference light will not exert any influence on the sample and that, hence, only the excitation light will actually pass through the sample. Due to the proposal according to the invention to separate the optical paths of the excitation light and the resulting fluorescence light from the reference light, an identical wavelength can be used according to the invention both for the excitation light and for the reference light, evaluation advantages will immediately result, since, as opposed to the known prior art, no different wavelength relative to the excitation light is used for the reference light in order to avoid any influence on the sample, so that cumbersome corrections, in particular in terms of ambient parameters such as, for instance, the temperature of the sample, while taking into account the different wavelengths can also be obviated. The method according to the invention, thus, enables simplified evaluation, in particular, to the effect that the same wavelength can be used both for the excitation light and for the reference light. Ambient influences to be compensated for, for instance, include changes caused by temperature changes or by tolerances of the respective components. In accordance with the invention, identically constructed light sources can, thus, be used both for exciting and referencing, which will ensure improved referencing, since both have identical optical and electric properties.

For the structurally simple separation of the optical paths, it is preferably proposed according to the invention that the separation of the optical paths is effected by an optical filter.

For a particularly reliable separation of the optical paths both for the excitation light and for the reference light, it is proposed according to a further preferred embodiment that the reference light is fed to the receiver through a light guide, whereby the use of such a light guide will ensure that no scattered light of the reference light will optionally enter the sample and, hence, influence the same.

As already pointed out above, a substantial characteristic feature of the present invention resides in that the excitation light and the reference light have identical wavelengths because of the appropriate separation of the optical paths proposed by the invention. To obtain such identical wavelengths, it is proposed by the invention, according to a further preferred embodiment, that the reference light is provided by a separate light source which is identical with that providing the excitation light.

To ensure a particularly reliable control and simplified subsequent evaluation, in particular, in regard to a phase shift, it is proposed according to a further preferred embodiment that the excitation light source and the reference light source are driven by a common modulator.

Instead of using two substantially identical light sources for providing the excitation light and the reference light, it is preferably proposed by the invention, according to an alternative embodiment, that the light emitted by the light source for emitting excitation light is switched between the optical path for the passage through the sample and the separate optical path of the reference light. Such an embodiment will, thus, do with a single light source by switching between the optical paths for the excitation light and the reference light. Evaluation in this respect will be facilitated in that the light source providing the excitation light and the reference light is identical such that also a reduction of the construction expenditures will be feasible, in particular by dispensing, for instance, with a common modulator or a more expensive driver circuit for the light source, since a usually simple changeover switch will be sufficient.

As already indicated above, the ratio of fluorescence light to excitation light is small, requiring an appropriate evaluation, amplification and signal processing known per se to follow the detection in the receiver, wherein, in this respect, it is proposed according to a further preferred embodiment that, in a manner known per se, the measurement signals emitted by the receiver are amplified in an amplifier and subsequently processed in a signal processing unit and optionally displayed.

To solve the initially mentioned objects, a device of the initially defined kind is, moreover, substantially characterized in that the optical path of the excitation light entering the sample and the fluorescence light leaving the sample is separated from the optical path of the reference light having the same wavelength as the excitation light, between the light source and the receiver. As already indicated above, the provision of separate optical paths both for the excitation light and the fluorescence light resulting therefrom after having passed through the sample and for the reference light enables the use of the same wavelength for both the excitation light and the fluorescence light such that the respective evaluation expenditures will, in particular, be simplified and reduced.

For a simple and reliable separation, it is proposed that an optical filter is used for the separation of the optical paths, as in correspondence with a preferred embodiment of the device according to the invention.

To provide an identical wavelength for both the reference light and the excitation light, it is contemplated according to a further preferred embodiment that two identical and separate light sources are provided for the generation of the light for irradiating the sample for the excitation of fluorescence and the production of the reference light.

For the reliable and simple control of the two identical light sources each providing the same wavelength for both the excitation light and the fluorescence light, it is, moreover, proposed in a preferred manner that a common frequency modulator is provided for the two light sources.

As likewise pointed out above, a single light source and a changeover switching device will do instead of the provision of two identical light sources, in which case subsequent evaluation will be further simplified and reduced, wherein, in this respect, it is proposed according to a further preferred embodiment that a light source is provided, downstream of which a changeover switching device is arranged for the supply of the light emitted by the light source to the sample and, alternatively, into the optical path of the reference light, thus enabling a reduction of the electronic expenditures involved.

For a particularly reliable spatial separation of the optical paths of the reference light and the excitation light, it is proposed according to a further preferred embodiment that a light guide, in particular a fiber cable, is provided for the supply of the reference light to the receiver.

In order to obtain accordingly strong and convincing signals, it is, moreover, proposed that, in a manner known per se, an amplifier and an evaluation and processing unit as well as, optionally, a display unit are arranged downstream of the receiver, as in correspondence with a further preferred embodiment of the device according to the invention.

In order to provide reliable light sources, which are also accordingly cost-effective to produce and mutually reconcilable, it is proposed according to a further preferred embodiment that the light source(s) is/are formed by a LED.

A preferred use of the method according to the invention and/or device according to the invention is in a bioreactor, in chemical and/or biochemical analytics or in medical diagnostics.

SHORT DESCRIPTION OF THE DRAWINGS

In the following, the invention will be explained in more detail by way of exemplary embodiments illustrated in the drawing. Therein:

FIG. 1 is a schematic illustration of a device for determining the fluorescence of a sample to be used for carrying out the respective method, according to the prior art;

FIG. 2, in an illustration similar to that of FIG. 1, depicts a first embodiment of a device according to the invention for determining the fluorescence of a sample to be used for carrying out the respective method;

FIG. 3 schematically illustrates the structural design of a device according to the invention using two separate light sources;

Figure 2:
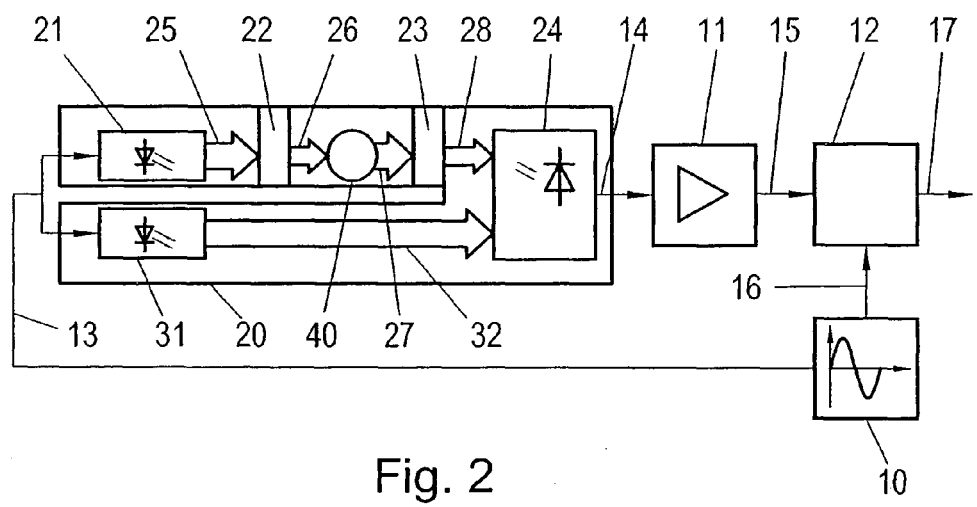
Figure 4:
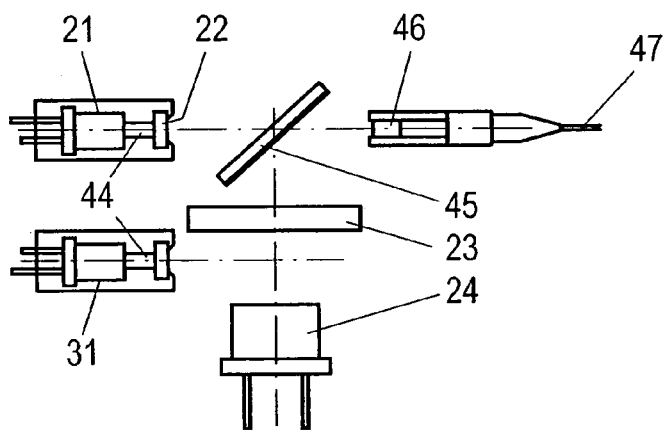
FIG. 4 depicts a modified embodiment of a device according to the invention using two separate light sources.
Figure 5:
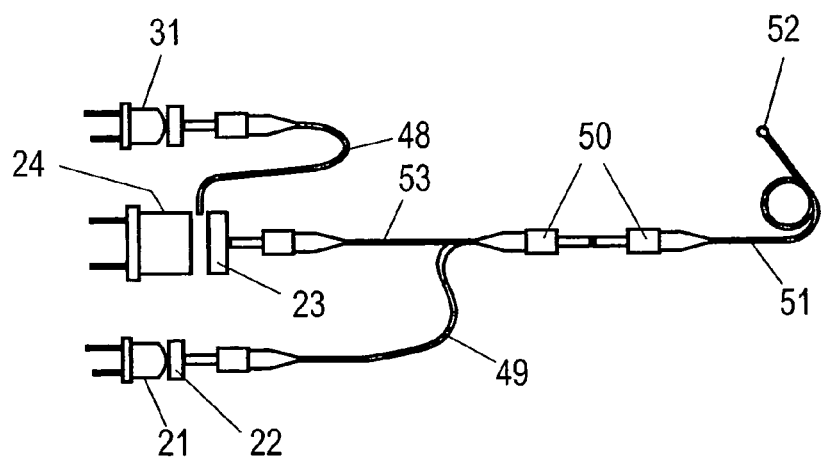
FIG. 5 depicts a further modified embodiment of a device according to the invention using two separate light sources.
Figure 6:
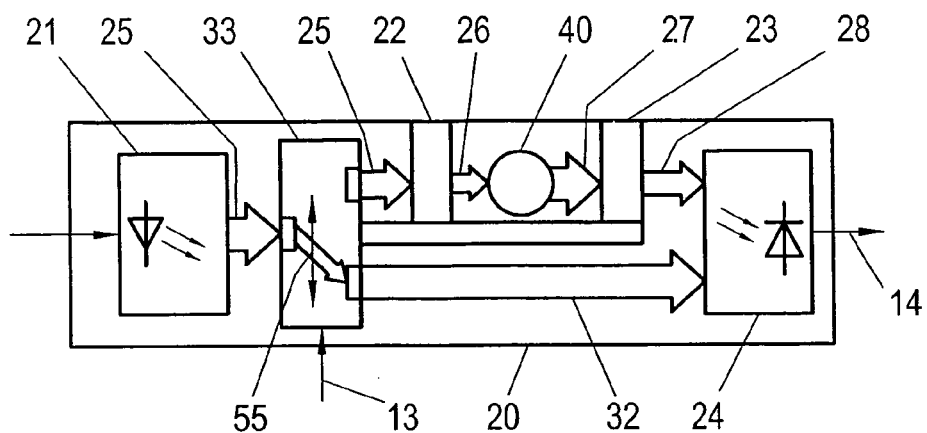
Figure 7:
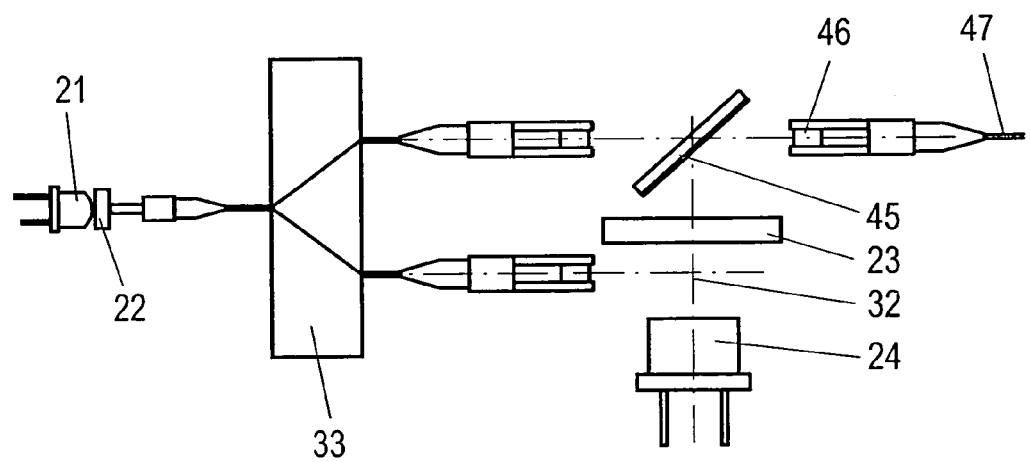

FIG. 6, in an illustration similar to that of FIG. 2, depicts a modified embodiment of the device according to the invention, using a common light source for the excitation light and the reference light as well as a turnover switch; and FIG. 7 is a schematic illustration similar to that of FIGS. 4 and 5, of an embodiment of a device according to the invention using a common light source and a turnover switch.

DETAILED DESCRIPTION OF PREFERRED EMBODIMENTS

Figure 1:
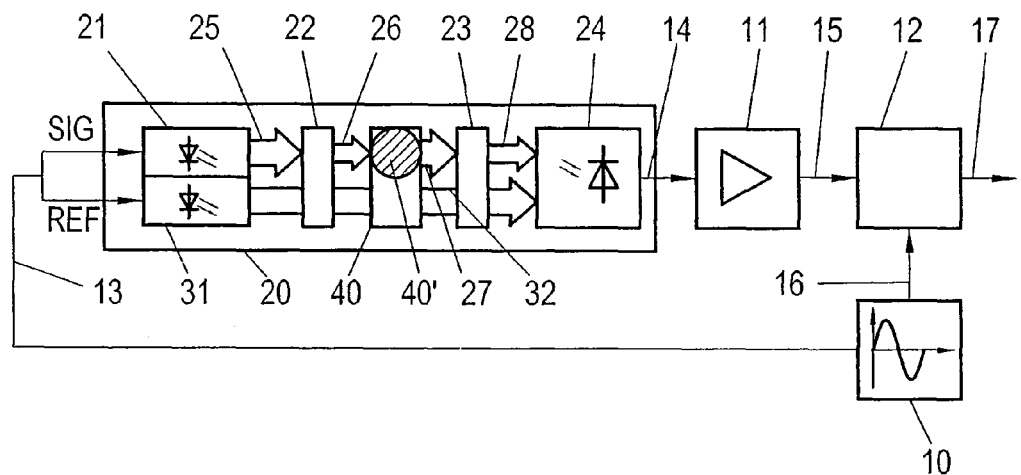

An embodiment according to the prior art, wherein both the excitation light and the reference light are passed through a sample 40, is illustrated in FIG. 1. A frequency modulator 10 generates a sinusoidal modulation signal having the frequency f0 13 to supply either an excitation light source 21 or a reference light source 31. The two light sources 21, 31 are integrated in an optical cell in such as manner as to largely prevent, by the aid of optical filters 22, 23 and suitable geometric arrangements, the excitation light 25 from reaching the optical receiver 24, while exciting the sample 40 as intensely as possible with the filtered excitation light 26. Furthermore, the optical filter 23 is selected such that the fluorescence light 27 is able to reach the detector as unhindered as possible. In the event of a reference measurement, the reference light 32 passes through the optical filter 23 to reach the detector, wherein it is to be taken care that no fluorescence be caused within the sample 40. It is, thus, the task of the optical filter 23 to separate the fluorescence light 27 as perfectly as possible from the excitation light 26, on the one hand, and to allow the reference light 32 having a different wavelength to pass through as unhindered as possible, on the other hand. In any case, in the optical receiver 24, the transformation of the incoming light into an electrical measuring signal 14 takes place, which is changed in an amplifier 11 in a manner that the amplified electric measuring signal 15 will be suitable for processing in an electronic signal processing means 12 so as to enable fluorescence data 17 to be generated from said measuring signal along with the electric reference signal 16.

Such a referencing method is based, for one part, on the separation of the optical excitation signal 26 and fluorescence signal 27 from the detector 24 by the optical filter 23 and, for the other part, on an adaptation as perfect as possible of the reference light source 31 to the excitation light source 21 in terms of electric properties and temperature behaviour, with a suitable geometric arrangement of the optical components having to be provided.

In FIG. 1, the subregion of the sample in which an excitation is effected by the excitation light so as to cause the subsequent emergence of the fluorescence light 28 is indicated by a hatched area 40'.

That known embodiment according to the prior art, in particular, involves the drawback that the excitation light of the light source 21 and the reference light of the light source 31 have different wavelengths so as to require additional compensation procedures to take into account ambient or environmental influences such as, for instance, the temperature at the different wavelengths of the excitation light 25 and the reference light 32. In doing so, a red and a green LED may, for instance, serve as light sources 21 and 31, respectively.

Since signal and reference are comprised of different LEDs 21 and 31, respectively, in terms of light emission, also different electric properties such as, e.g., junction capacity, temperature behaviour etc. will physically result, thus deteriorating the quality of referencing.

In the embodiment according to the invention depicted in FIG. 2, the reference numerals for identical components of the embodiment according to FIG. 1 have been retained. It is, in particular, apparent that the excitation light 25 provided by the light source 21, similarly to the embodiment according to FIG. 1, subsequently passes through the filter 22 and the sample 40 in which an excitation occurs, whereupon the fluorescence light 27 emerges and reaches the filter 23, whereupon it is again fed to the detector or optical receiver 24 as a filtered fluorescence light 28.

The separation between the excitation light 25 and the fluorescence light 27 and 28 resulting after the passage through the sample, from the reference light 32 is effected in that the filter 23 is configured for the spatial separation of the light paths 26, 27 and 28 as well as 32. In this respect, it is ensured that no reflection of the reference light 23 to the sample 40 will occur, which would excite the same and cause the emission of fluorescence light 27. The design of the optical filter 23 must prevent any transmission of reference light 32 to the sample, any transmission of excitation light 26 to the optical receiver 24, yet, to a high degree, must allow the transmission of fluorescence light 27 to the optical receiver 24.

The evaluation of the signals received in the optical receiver or detector 24 is performed as in the embodiment according to the prior art in FIG. 1, by the consecutively arranged amplifier 11, the electronic signal processing unit 12 as well as an optional data display, which is again indicated by 17.

The advantage of the embodiment according to FIG. 2 resulting from the provision of an optical path separation primarily resides in that two identical light sources 21 and 31 can be used so as to facilitate referencing and evaluating, or enable the same to be effected more precisely as compared to the prior art according to FIG. 1, since additional influences by the use of two different light sources having different wavelengths as in accordance with the prior art, and the consequent optionally additionally required compensations will be avoided.

Figure 3:
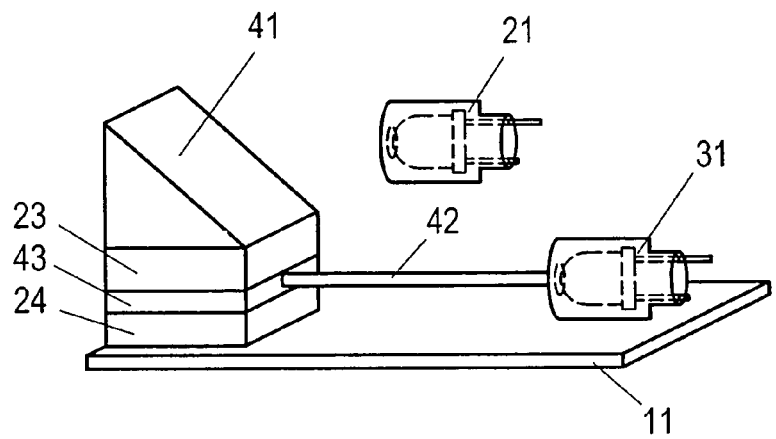

From the embodiment illustrated in FIG. 3, which is based on the schematic diagram of FIG. 2, it is apparent that the light source 21 formed, for instance, by a LED directs its light to a prism 41, with a sample (not illustrated) being arranged downstream of said prisms 41.

By contrast, light from the light source 31 for providing the reference light is fed via a fiber cable 42 to an element 43 formed by a glass plate and interposed between the signal light and the reference light, from the prism 41 through the filter 23 for separating the optical paths, whereby the reference light fed by the fiber cable 42 is directly supplied to the detector or optical receiver 24, with a consecutively arranged preamplifier being again denoted by 11.

From the modified embodiment according to FIG. 4, it is apparent that excitation light provided by the light source again denoted by 21, which passes through the excitation filter 22 after having passed a so-called Grin lens 44, travels through a dichroic filter 45 and, after having passed through another Grin lens 46, is supplied to a sensitive layer, or sample to be examined, which is schematically indicated by 47. The fluorescence light emitted by the sample 47 is fed via the dichroic filter 45 to the light detector or optical receiver 24 after having passed through an emission filter again denoted by 23.

By contrast, the supply of reference light provided by the light source 31 takes place directly to the light detector 24, wherein a filter 23 is again used to separate the optical paths.

FIG. 5 depicts a further modified embodiment using two identical light sources 21 and 31, wherein the light source 31 for providing the reference light is directly coupled with the optical receiver or detector again denoted by 24, via a light guide 48.

By contrast, light provided by the excitation light source 21, after having passed through the filter 22, is supplied to the sample 52 to be examined, for instance an $O_2$-sensitive layer, likewise via a light guide 49 and schematically indicated couplings 50 and, subsequently, via a further light guide 40 and schematically indicated couplings 50. Via the light guides 51 and 53, fluorescence light is again supplied to the detector or optical receiver 24 after having passed through the emission filter 23.

FIG. 6 depicts a modified embodiment using but a single light source, which is again denoted by 21, from which light denoted by 25 is supplied to a turnover switching device or turnover switch 33. This turnover switch either causes the propagation of the excitation light provided by the light source 21 to the filter 22 and, after this, into the sample 40, from which fluorescence light 27 emerges to be supplied as fluorescence light 28 to the optical receiver or optical detector again denoted by 24, for further processing after having passed through the filter 23.

As indicated in FIG. 6 by double arrow 55, a switchover is again effected in the turnover switching device 33 between the light path of the excitation light 25 through the sample 40 and a path again denoted by 23 of the reference light, which is directly supplied to the optical receiver or optical detector 24.

In FIG. 6, the coupling with a driver circuit or frequency modulator (not illustrated) is again denoted by 13.

The advantage of this embodiment primarily resides in that just a single light source 21 will do, thus also requiring but a single driver circuit. Hence result reduced expenditures by the omission of the separate reference light source such that a more precise evaluation will be achieved, in particular, by the elimination of optionally existing component differences of identical light sources as are, for instance, denoted by 21 and 31 in FIG. 2. This increase in accuracy in most cases outweighs the additional expenditures entrained by the provision of the turnover switching device of turnover switch 33.

From the illustration according to FIG. 7, it is apparent that the light beam, after having passed through an excitation filter 22, is provided to the turnover switching device of turnover switch 33, wherein the light, on the optical path 32 of the reference light, is again directly supplied to the detector or optical receiver 24.

On the other hand, the excitation light, after having passed through a dichroic filter again denoted by 45, is supplied to a sensitive layer again denoted by 47 in a manner similar to that of the embodiment according to FIG. 4. The fluorescence light formed within the same is again supplied to the light detector or optical receiver 24 after having passed through the dichroic filter 45 and the emission filter 23.

It is apparent that, in particular, by providing just a single light source 21, the construction expenditures can be reduced while achieving enhanced evaluation accuracy.

A preferred application of the embodiments illustrated in FIGS. 2 to 7 is, for instance, in a bioreactor, in chemical and/or biochemical analytics or in medical diagnostics.

The invention claimed is:

1. A method for determining the fluorescence of a sample, wherein the sample is irradiated with light of a wavelength which is suitable to excite fluorescent light in the sample, and the fluorescence light emitted by the sample is received in a receiver and converted into a measurement signal, wherein reference light, in particular for compensating for ambient influences, is additionally fed to the receiver and likewise converted into a reference measurement signal, wherein that the optical path of the excitation light entering the sample and the fluorescence light leaving the sample is separated from the optical path of the reference light having the same wavelength as the excitation light, between the light sources and the receiver, and wherein the reference light is provided by a separate light source which is identical with that providing the excitation light.

2. The method according to claim 1, wherein the separation of the optical paths is effected by an optical filter.

3. The method according to claim 1, wherein the reference light is fed to the receiver through a light guide.

4. The method according to claim 1, wherein the excitation light source and the reference light source are driven by a common modulator.

5. The method according to claim 1, wherein in a manner known per se, the measurement signals emitted by the receiver are amplified in an amplifier and subsequently processed in a signal processing unit and optionally displayed.

6. The use of the method according to claim 1 in a bioreactor, in chemical and/or biochemical analytics or in medical diagnostics.

7. A device for determining the fluorescence of a sample, including a light source for emitting light of a wavelength which is suitable to excite fluorescent light in the sample, and a receiver which receives the fluorescence light emitted by the sample and converts the same into a measurement signal, wherein reference light, in particular for compensating for ambient influences, is additionally feedable to the receiver and convertible into a reference measurement signal by the same, wherein the optical path of the excitation light entering the sample and the fluorescence light leaving the sample is separated from the optical path of the reference light having the same wavelength as the excitation light, between the light source and the receiver, and wherein two identical and separate light sources are provided for the generation of the light for irradiating the sample for the excitation of fluorescence and the production of the reference light.

8. The device according to claim 7, wherein an optical filter is used for the separation of the optical paths.

9. The device according to claim 7, wherein a common frequency modulator is provided for the two light sources.

10. The device according to claim 7, wherein a light guide, in particular a fiber cable, is provided for the supply of the reference light to the receiver.

11. The device according to claim 7, wherein, in a manner known per se, an amplifier and an evaluation and processing unit as well as, optionally, a display unit are arranged downstream of the receiver.

12. The device according to claim 7, wherein that the light sources are formed by a LEDs.

13. The use of the device according to claim 7 in a bioreactor, in chemical and/or biochemical analytics or in medical diagnostics.

* * * * *